United States Patent
Bhalla et al.

(10) Patent No.: US 7,799,788 B2
(45) Date of Patent: Sep. 21, 2010

(54) METHOD OF TREATING CHRONIC MYELOGENOUS LEUKEMIA CELLS

(75) Inventors: Kapil N. Bhalla, Tampa, FL (US); Francis Y. Lee, Yardley, PA (US)

(73) Assignees: University of South Florida, Tampa, FL (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/364,009

(22) Filed: Feb. 2, 2009

(65) Prior Publication Data
US 2009/0215792 A1    Aug. 27, 2009

Related U.S. Application Data

(63) Continuation of application No. PCT/US2007/075061, filed on Aug. 2, 2007.

(60) Provisional application No. 60/821,184, filed on Aug. 2, 2006.

(51) Int. Cl.
*A61K 31/497*    (2006.01)

(52) U.S. Cl. .................................. 514/252.14

(58) Field of Classification Search ............ 514/252.14
See application file for complete search history.

(56) References Cited

U.S. PATENT DOCUMENTS 6,987,103 B2    1/2006   Robin et al.

2005/0209186 A1    9/2005   Lyons

OTHER PUBLICATIONS

Fiskus, W., et al. "Combined Effects of Novel Tyrosine Kinase Inhibitor AMN107 and Histone Deacetylase Inhibitor LBH589 Against Bcr-Abl-Expressing Human Leukemia Cells." Blood. 2006. vol. 108, No. 2, pp. 645-652.

Kelly, William et al. "Histone Deacetylase Inhibitors: From Target to Clinical Trials." Expert Opin. Investig. Drugs, 2002, vol. 11, No. 12, pp. 1695-1713.

Nimmanapalli, Ramadevi, et al. "Cotreatment with the Histone Deacetylase Inhibitor Suberoylanilide Hydroxamic Acid (SAHA) Enhances Imatinib-Induced Apoptosis of Bcr-Abl-Positive Human Acute Leukemia Cells." Blood. 2003. vol. 101, No. 8, pp. 3236-3239.

O'Hare, Thomas, et. al. "In Vitro Activity of Bcr-Abl Inhibitors AMN107 and BMS-354825 Against Clinically Relevant Imatinib-Resistant Abl Kinase Domain Mutants." 2005. vol. 65, No. 11, pp. 4500-4505.

*Primary Examiner*—Raymond J Henley, III
(74) *Attorney, Agent, or Firm*—Michele L. Lawson; Smith & Hopen, P.A.

(57) ABSTRACT

Here, the inventors disclose the treatment of imatinib mesylate resistant chronic myelogenous leukemia cells with a cotreatment of vorinostat (SAHA, suberoylanilide hydroxamic acid) and dasatinib, a dual Abl/Src kinase (TK) inhibitor. Combined treatment of cultured human CML and BaF3 cells with vorinostat and dasatinib induced more apoptosis than either agent alone, as well as synergistically induced loss of clonogenic survival, which was associated with greater depletion of Bcr-Abl, p-CrkL and p-STAT5 levels. Co-treatment with dasatinib and vorinostat also attenuated the levels of Bcr-AblE255K and Bcr-AblT315I and induced apoptosis of BaF3 cells with ectopic expression of the mutant forms of Bcr-Abl. Finally, co-treatment of the primary CML cells with vorinostat and dasatinib induced more loss of cell viability and depleted Bcr-Abl or Bcr-AblT315I, p-STAT5 and p-CrkL levels than either agent alone.

20 Claims, 11 Drawing Sheets

K562 cells

|  | G0/G1 | S | G2/M |
| --- | --- | --- | --- |
| Control | 39.3 ± 6.0 | 53.1 ± 1.6 | 7.6 ± 4.7 |
| 2 nM, dasatinib | 78.5 ± 7.6 | 20.7 ± 6.3 | 0.9 ± 1.2 |
| 2 µM, vorinostat | 86.5 ± 5.6 | 8.6 ± 3.6 | 5.0 ± 2.3 |
| dasatinib + vorinostat | 89.3 ± 8.3 | 9.5 ± 7.0 | 1.1 ± 1.1 |

FIGURE 6

| Sample | Untreated | 2 nM. dasatinib | 5 nM. dasatinib | 10 nM. dasatinib | 2 µM. vorinostat | 2 nM. dasatinib + vorinostat | 5 nM. dasatinib + vorinostat | 10 nM. dasatinib + vorinostat |
|---|---|---|---|---|---|---|---|---|
| #1 | 2.2 | 12.4 | 23.9 | 33.0 | 41.6 | 46.7 | 56.4 | 63.5 |
| #2 | 5.0 | 20.8 | 22.1 | 27.5 | 57.9 | 64.6 | 64.4 | 77.8 |
| #3 | 14.6 | 24.6 | 24.0 | ND | 30.4 | 44.0 | 45.7 | ND |
| #4 | 12.8 | 44.5 | 49.7 | 53.8 | 76.2 | 93.1 | 91.6 | 96.0 |
| #5 | 15.0 | 32.6 | 42.7 | 46.3 | 43.5 | 48.3 | 53.6 | 56.8 |
| #6 | 10.6 | 12.0 | 13.9 | 15.8 | 38.0 | 39.2 | 38.0 | 44.7 |
| #7 | 4.2 | 10.2 | 11.6 | 12.4 | 17.8 | 24.3 | 23.4 | 24.4 |
| #8 | 8.8 | 11.3 | 18.0 | 18.0 | 30.9 | 30.0 | 32.75 | 35.0 |
| #9 | 6.1 | 8.9 | 10.8 | 16.7 | 12.3 | 19.6 | 24.4 | 27.3 |
| #10* | 13.7 | 27.4 | 28.0 | 32.5 | 35.1 | 35.4 | 40.6 | 42.5 |
| #11* | 14.7 | 19.9 | 19.8 | 19.8 | 48.1 | 47.0 | 47.2 | 45.7 |

US 7,799,788 B2

METHOD OF TREATING CHRONIC MYELOGENOUS LEUKEMIA CELLS

CROSS REFERENCE TO RELATED APPLICATIONS

This application is a continuation of prior filed International Application, Serial Number PCT/US2007/075061 filed Aug. 2, 2007, which claims priority to U.S. provisional patent application No. 60/821,184 filed Aug. 2, 2006 which is hereby incorporated by reference into this disclosure.

BACKGROUND OF THE INVENTION

The fusion oncogene bcr-abl encoded Bcr-Abl tyrosine kinase (TK) activates many pro-growth and cell survival mechanisms, which confer resistance to apoptosis. These include increased phosphorylation and transactivation by STAT-5 (signal transducer and activator of transcription), which leads to increased expression of the anti-apoptotic $Bcl-x_L$ and Pim-2 protein, as well as increased Ras/Raf/MEK/ERK1/2, AKT and NFκB activity. Through deregulated AKT activity, Bcr-Abl inhibits the Forkhead transcription regulator FOXO3a, which leads to depletion of the cyclin-dependent kinase-2 inhibitor p27 and the BH3 domain-only-containing pro-apoptotic Bim protein. Collectively, these molecular perturbations promote cell proliferation and survival and contribute to Bcr-Abl-mediated leukemia transformation of bone marrow progenitor cells. Clinical studies have shown that Bcr-Abl TK remains a therapeutic target in all phases of CML. Although highly active in inducing clinical and cytogenetic complete remissions in many CML patients, resistance to imatinib mesylate (IM, Gleevec®) is an increasing clinical problem in CML, especially in the accelerated phase (AP) and blast crisis (BC) phase where only short-term responses are observed.

The major mechanisms of resistance to IM include mutations in the kinase domain of bcr-abl, amplification of the bcr-abl gene, as well as Bcr-Abl-independent mechanisms of resistance. Within the Bcr-Abl kinase domain, close to 40 known point mutations have been described. These have been linked to IM resistance in CML. The mutations are of two broad categories: those that directly interfere with the ability of IM to bind to the kinase domain (e.g., T315I), and those that impair the ability of Bcr-Abl to achieve inactive conformation required for binding to IM, (e.g., E255K, P-loop mutation). Bcr-Abl mutations impart varying degrees of resistance to IM. Some remain susceptible to higher concentrations of IM, while others that interfere directly with the binding of Bcr-Abl to IM (e.g. T315I, involving the gatekeeper threonine residue) confer the highest form of resistance to IM. These findings highlight the need to develop and test novel anti-Bcr-Abl agents that are more potent than IM and/or are able to override the resistance to IM due to either mutations or amplifications of Bcr-Abl.

BMS-354825 (dasatinib) is a synthetic, small molecule, thiazole-based, orally-bioavailable, ATP-competitive, dual Abl/Src kinase inhibitor. Dasatinib has been shown to inhibit the activity of the Src kinase family members c-Src and Lyn. Dasatinib is able to bind the active and inactive conformations of Abl and inhibits the tyrosine kinase activity of Bcr-Abl. Dasatinib is approximately 325-fold more potent than IM in inhibiting the activity of Bcr-Abl. CrkL is a 39 kDa, tyrosine phosphorylated adaptor protein, which is involved in hematopoietic and leukemia cell signaling and is an important substrate of Bcr-Abl. Inhibition of Bcr-Abl activity in CML cells has been gauged by the decline in the levels of phosphorylated CrkL. Importantly, in vitro studies have shown that dasatinib is also able to inhibit most clinically significant IM-resistant mutant isoforms of Bcr-Abl, but is ineffective against Bcr-Abl T315I due to steric hindrance caused by the sidechain of the isoleucine. Dasatinib prolongs the survival of mice with IM-resistant, Bcr-Abl-dependent leukemia, but the drug was ineffective against tumors expressing the mutant Bcr-AblT315I. In Phase I and early Phase II studies, dasatinib has been reported to induce complete hematologic and cytogenetic responses in patients with IM-resistant or IM-intolerant chronic phase of CML. However, the responses are significantly lower in patients with more advanced phases of CML.

Vorinostat (SAHA; suberoylanilide hydroxamic acid) is a hydroxamic acid based polar histone deacetylase inhibitor. Treatment with hydroxamic acid analogue (HA) histone deacetylase inhibitors (HDIs) leads to increased levels of genes involved in cell cycle regulation such as p21 and p27, generation of reactive oxygen species (ROS), induction of TRAIL and its death receptors, as well as upregulation of the levels of the pro-death proteins, e.g., Bax, Bak and Bim. These agents are also known to deplete the levels of anti-apoptotic proteins e.g., Bcl-2, $Bcl-x_L$, XIAP, survivin, AKT and Pim-2, in human leukemia cells. Collectively, these effects inhibit cell-cycle growth, lower the threshold to apoptotic stimuli and induce apoptosis of CML cells. Recent studies from the inventor's laboratory have demonstrated that treatment with the HA-HDIs, e.g., vorinostat, LAQ824 and LBH589, alone also depleted Bcr-Abl, as well as induced apoptosis and sensitized Bcr-Abl expressing leukemia cells to apoptosis induced by IM. By inducing acetylation of hsp90 through inhibition of HDAC6, treatment with HA-HDIs was shown to inhibit the ATP-binding and chaperone function of hsp90. This led to polyubiquitylation, proteasomal degradation and depletion of hsp90 client proteins, including Bcr-Abl, c-Raf and AKT. Significantly, the inventor's studies also showed that treatment with HA-HDIs reduced the levels of the highly IM-refractory Bcr-AblT315I and induced apoptosis of primary IM-refractory CML-BC cells.

SUMMARY OF INVENTION

Resistance to imatinib mesylate (IM) in chronic myeloid leukemia (CML) is commonly due to mutations in the kinase domain of Bcr-Abl. Dasatinib (Bistol-Myers Squibb, Co.) is a highly potent, oral, multi-targeted kinase inhibitor that inhibits wild-type (WT) and most IM-resistant mutants (mt) of Bcr-Abl, except T315I. Here, the inventors disclose the surprising anti-leukemic effects of dasatinib in combination with vorinostat, against mouse or human, cultured or primary, WT or mt Bcr-Abl-expressing leukemia cells. Dasatinib (2.0 to 20 nM for 24 to 48 hours) induced a dose-dependent increase in the percentage of cells in G1 phase of the cell cycle and apoptosis of K562 and LAMA-84 cells. This was associated with marked increase in p27 expression, but a decline in Bcr-Abl auto-phosphorylation and p-CrkL, p-STAT5, p-Akt and Bcl-xL levels, without significant change in Bcr-Abl levels.

Treatment with 5 to 20 nM dasatinib induced apoptosis of mouse bone marrow BaF3 cells rendered IL-3 independent for growth by ectopic expression of IM-sensitive WT Bcr-Abl (BaF3/WT-Bcr-Abl cells) or the P-loop mutant (BaF3/Bcr-Abl-E255K cells). This was associated with decline in auto-phosphorylated Bcr-Abl, p-CrkL and p-STAT5 levels. In contrast, dasatinib was inactive against the highly IM-resistant T315I Bcr-Abl mutant. However, treatment with vorinostat (0.5 to 2.0 µM) induced apoptosis of not only BaF3/WT- and BaF3/Bcr-Abl-E255K, but also of BaF3/Bcr-Abl-T315I cells in a dose-dependent manner. This was associated with attenuation of the levels and auto-phosphorylation of WT and mutant Bcr-Abl.

Co-treatment with dasatinib (2.0 to 20 nM) and vorinostat (2.0 µM) induced surprisingly more apoptosis of BaF3/WT-Bcr-Abl and BaF3/Bcr-Abl-E255K cells than treatment with either agent alone. The apoptotic effect of the combination was also associated with attenuation of WT and mt Bcr-Abl auto-phosphorylation. Additionally, co-treatment with dasatinib and vorinostat, versus either agent alone, induced more apoptosis of primary CML cells (5 samples) derived from patients with IM-resistant CML cells, including a sample of cells documented to have the Bcr-Abl-T315I mutation.

In a first embodiment, the invention includes a method of inducing apoptosis in a cell by contacting the cell with a therapeutically effective amount of a dual Abl/Src kinase inhibitor and a histone deacetylase inhibitor. In a preferred embodiment, the dual Abl/Src kinase inhibitor is BMS-354825 (dasatinib) and the histone deacetylase inhibitor is Suberoylanalide Hydroxamic Acid (SAHA). In the preferred embodiment, the therapeutically effective amount of the Abl/Src kinase inhibitor is between about 2.0 to 20 nM and the therapeutically effective amount of Suberoylanalide Hydroxamic Acid is about 2.0 µM.

The combination disclosed is shown to have unexpected results in inducing apoptosis in chronic myelogenous leukemia (CML) cells, particularly where the CML cell is in accelerated phase or blast crisis phase.

It is therefore an object of the invention to provide a treatment for CML cells that are resistant to imatinib mesylate (IM).

It is another object of the invention to provide a treatment wherein dasatinib is combined with agents, such as suberoylanalide hydroxamic acid (SAHA), that are active against not only IM-resistant mutant forms of Bcr-Abl but are also effective in overriding non-Bcr-Abl dependent mechanisms of IM resistance.

It is yet another object of the invention to provide an enhanced treatment for cells containing a point mutation in the kinase domain of the bcr-abl gene. In a preferred embodiment, the point mutation in the kinase domain of Bcr-Abl is selected from the group consisting of T315I and E255K.

BRIEF DESCRIPTION OF THE DRAWINGS

For a fuller understanding of the invention, reference should be made to the following detailed description, taken in connection with the accompanying drawings, in which:

FIG. 6. Dasatinib and/or vorinostat induces loss of viability of primary CML-BC cells. Peripheral blood or bone marrow from nine imatinib mesylate resistant or refractory patients and two samples with mutant Bcr-AblT315I (indicated with an *) were treated with the indicated doses of dasatinib and/or vorinostat for 48 hours. Following this, the percentages of non-viable cells for each drug alone or drug combination were determined by trypan blue uptake in hemocytometer. Values represent the percentage of non-viable cells from each condition as compared to untreated cells.

DETAILED DESCRIPTION OF THE PREFERRED EMBODIMENT

The invention includes methods that override primary or acquired mechanisms of resistance in advanced phases of CML. The inventors show surprising results when dasatinib is combined with agents, such as suberoylanalide hydroxamic acid (SAHA), that are active against not only IM-resistant mutant forms of Bcr-Abl but are also effective in overriding non-Bcr-Abl dependent mechanisms of IM resistance.

Here the inventors show unexpected results for the efficacy of the combination of dasatinib and vorinostat against cultured and primary, IM-sensitive or -resistant, human CML cells, including those that expressed Bcr-AblT315I. The inventors also demonstrate similar effects of the combination against mouse pro-B BaF3 cells with ectopic expression of the unmutated Bcr-Abl or Bcr-AblE255K and Bcr-AblT315I.

Dasatinib inhibits Bcr-Abl, c-Src and Lyn tyrosine kinase activities and induces apoptosis of K562 and LAMA84 cells.

Figure 1A:
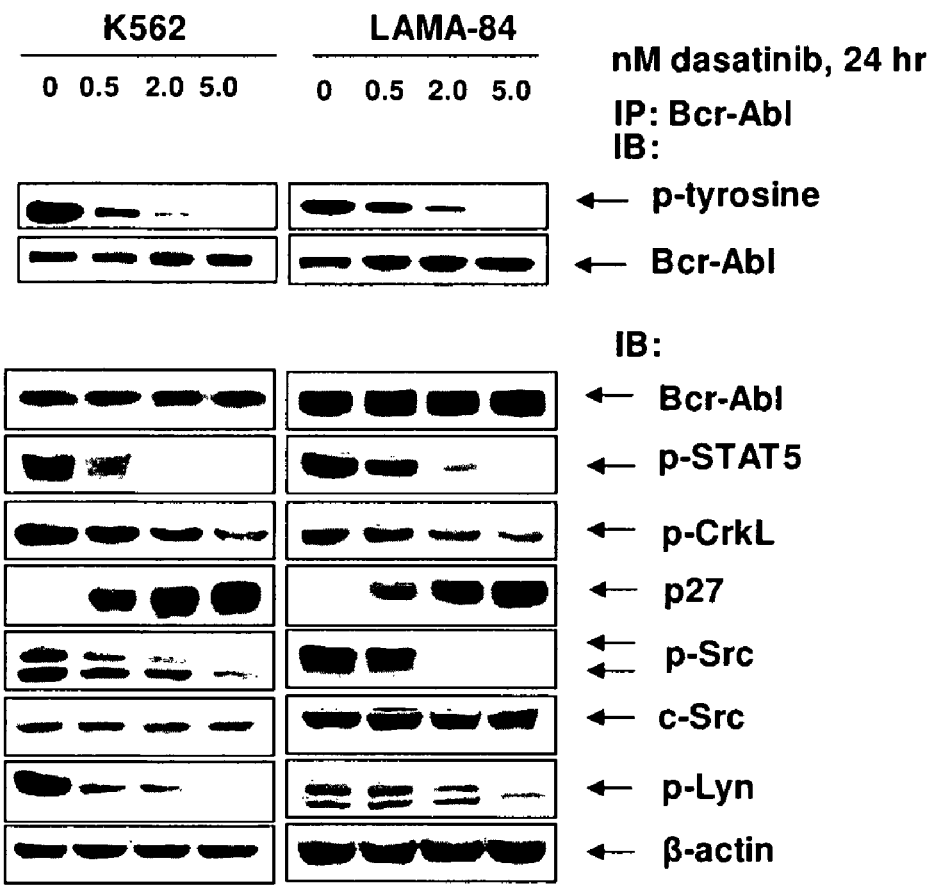
FIG. 1A. K562 and LAMA84 cells were treated with the indicated concentrations of dasatinib for 24 hours. Following this, Bcr-Abl was immunoprecipitated from total cell lysates and Western blot analysis was performed for tyrosine-phosphorylated Bcr-Abl. The blot was stripped and probed for total Bcr-Abl levels. Immunoblot analysis was performed for Bcr-Abl, p-STAT5, p-CrkL, p27, Bcl-$x_L$, p-Src (Tyr416), p-Lyn, and c-Src from the same lysates. The level of β-actin served as the loading control.
Figure 1B:
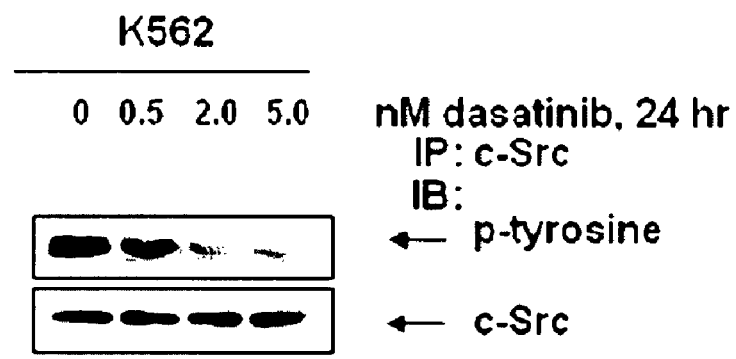
FIG. 1B. Results of Western Blot analysis. K562 cells were treated with the indicated concentrations of dasatinib (0 to 5.0 nM) for 24 hours. The results show that exposure to low nanomolar concentrations of dasatinib inhibits the autophosphorylation of Bcr-Abl and c-Src.

As a dual Abl/Src kinase inhibitor, dasatinib is a significantly more potent inhibitor of unmutated Bcr-Abl than Imatinib (IM), and is able to inhibit the activity of nearly all of the mutant forms of Bcr-Abl. Although dasatinib has been demonstrated to inhibit ectopically expressed unmutated and mutated Bcr-Abl, the kinase inhibitory effects of dasatinib have not been documented against endogenous Bcr-Abl and c-Src in human CML cells. Therefore, the inventors first determined the kinase inhibitory, cell cycle and apoptotic effects of dasatinib in the cultured CML K562 and LAMA-84 cells. FIGS. 1A and 1B clearly demonstrate that exposure to low nanomolar concentrations of dasatinib inhibits the auto-phosphorylation of Bcr-Abl and c-Src, as well as depletes the kinase activity of the immunoprecipitated c-Src and Lyn, as measured by the decrease in the phosphorylation of the Gab1CT substrate in the in vitro kinase assay.

Figure 1C:
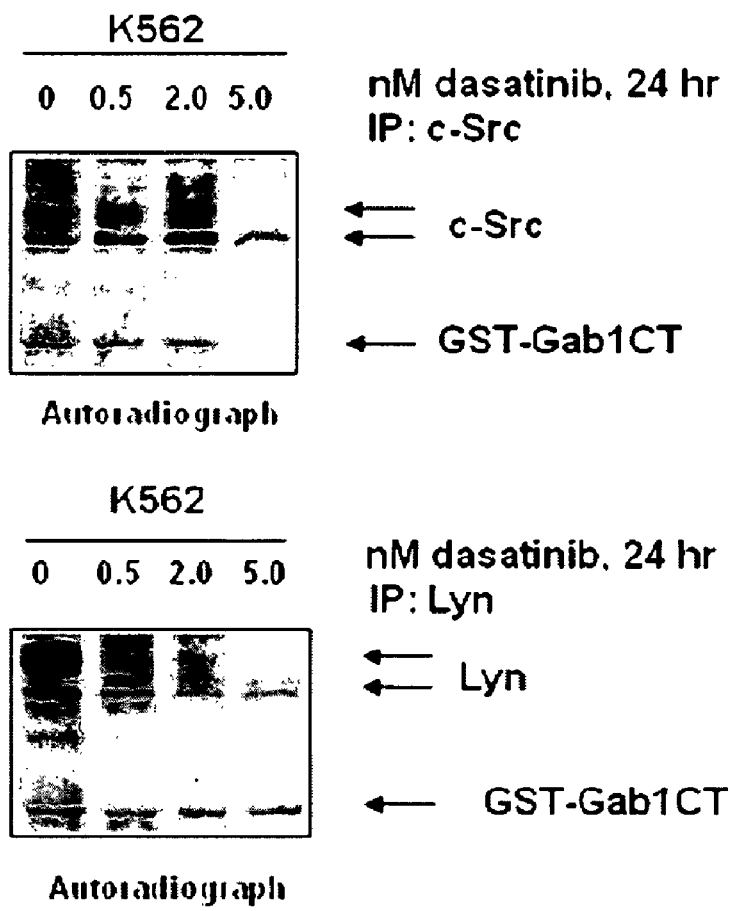
FIG. 1C. K562 cells were treated with the indicated concentrations of dasatinib for 24 hours. Following this, c-Src and Lyn were immunoprecipitated separately from the same cell lysates. Src and Lyn kinase assays were performed in the presence of [$\gamma$-$^{32}$P]ATP. After the kinase reactions, proteins were resolved by SDS-PAGE and transferred to nitrocellulose membranes. Autophosphorylation of Src or Lyn and phosphorylation of an exogenous substrate (Gab1CT) were visualized by autoradiography.
Figure 1D:
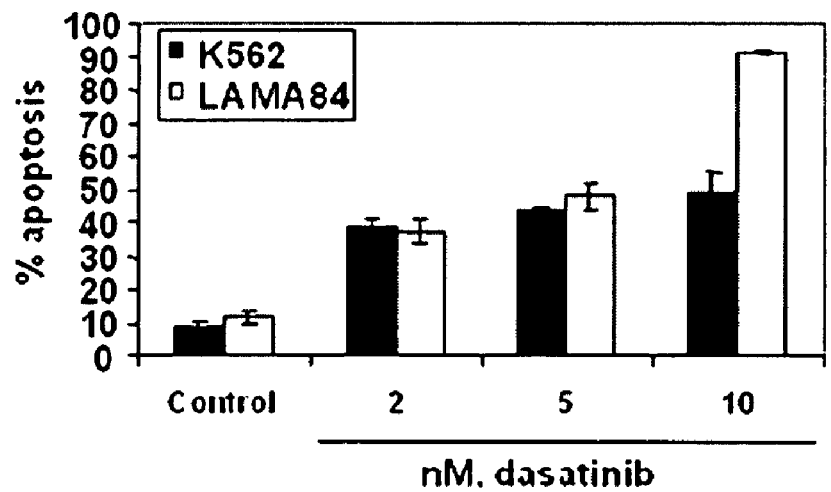
FIG. 1D. K562 and LAMA-84 cells were treated with the indicated concentrations of dasatinib for 48 hours. Following treatment, the percentages of annexin-V-stained apoptotic cells were measured by flow cytometry. Values represent the mean of three experiments±S.E.M.

Concomitantly, dasatinib attenuated the intracellular levels of p-STAT5, p-CrkL, p-Src and p-Lyn in a dose dependent manner. This was accompanied by a striking increase in p27 but decline in the levels of c-Myc and Bcl-$x_L$, which are transactivated by STAT5. No significant change occurred in the levels of Bcr-Abl and c-Src, or of Lyn, STAT-5 and CrkL. Exposure to 2.0 to 10 nM of dasatinib also induced apoptosis of K562 and LAMA-84 in a dose dependent manner, with approximately 90% apoptosis of LAMA-84 and 50% apoptosis of K562 cells at the 10 nM concentration of dasatinib (FIG. 1C).

Co-treatment with vorinostat and dasatinib exerts synergistic effects in K562 and LAMA-84 cells.

Figures 2A, 2B:
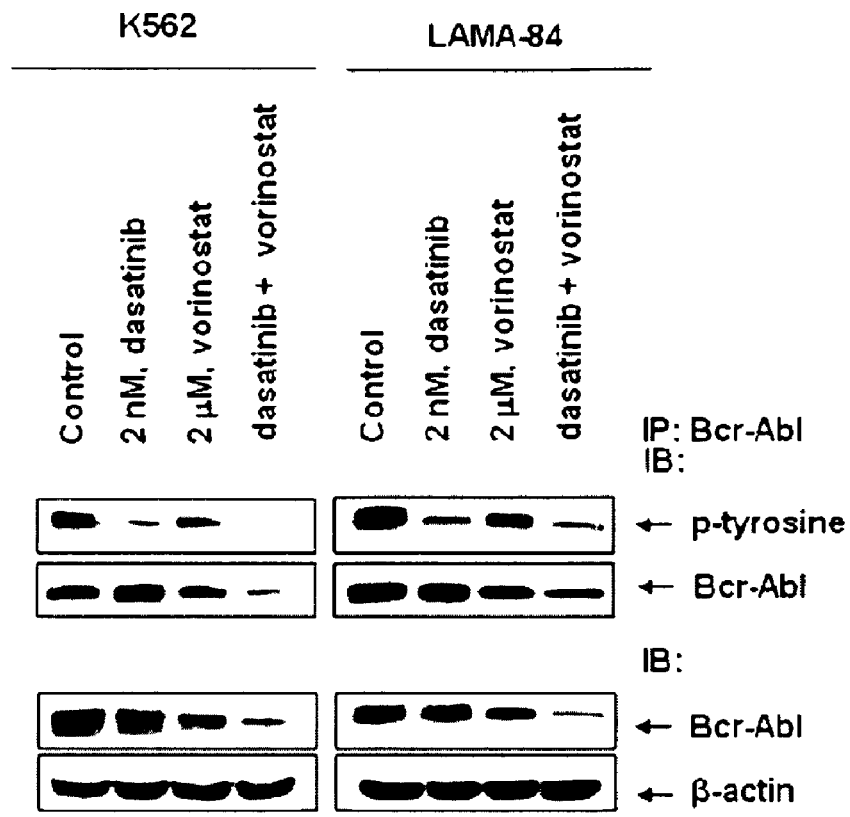
FIG. 2A. K562 and LAMA-84 cells were treated with the indicated concentrations of dasatinib and/or vorinostat for 24 hours. Bcr-Abl was immunoprecipitated from the total cell lysates and Western blot analysis was performed for tyrosine-phyosphorylated Bcr-Abl. The blot was stripped and probed for total Bcr-Abl levels. Immunoblots were performed for Bcr-Abl levels on the same cell lysates. The levels of β-actin served as the loading control.
FIG. 2B. K562 cells were treated with dasatinib and/or vorinostat for 24 hours. Cells were fixed and stained for cell cycle analysis by flow cytometry. The results showed a marked accumulation of the cells in the G1 phase and concomitant decline in the % of cells in the S phase of the cell cycle FIG. 2C. Analysis of dose effect relationship for dasatinib (1-5 nmol/L) and vorinostat (1-5 µmol/L) for the apoptotic effects after 48 hours of exposure was performed according to the median effect of Chou and Talalay. Following this the combination index values were calculated. CI<1, CI=1, and CI>1 represent synergism, additivity, and antagonism of the two agents, respectively.

In a previous report the inventors demonstrated that treatment with vorinostat attenuates Bcr-Abl, AKT and c-Raf levels and induces cell cycle growth arrest and apoptosis of CML cells. Additionally, vorinostat was shown to sensitize CML cells to apoptosis induced by IM. Next, the inventors determined the effects of the combined treatment with vorinostat and dasatinib on cell cycle status, apoptosis and clonogenic survival of K562 and LAMA-84 cells. As compared with the treatment with vorinostat or dasatinib alone, co-treatment with vorinostat and dasatinib caused surprisingly more depletion of the levels of auto-phosphorylated Bcr-Abl (FIG. 2A). Treatment with vorinostat and dasatinib also attenuated Bcr-Abl levels more than treatment with vorinostat alone (FIG. 2A). This was accompanied by marked accumulation of the cells in the G1 phase and concomitant decline in the % of cells in the S phase of the cell cycle (FIG. 2B), again more with the combination than with either agent alone.

Figure 2C:
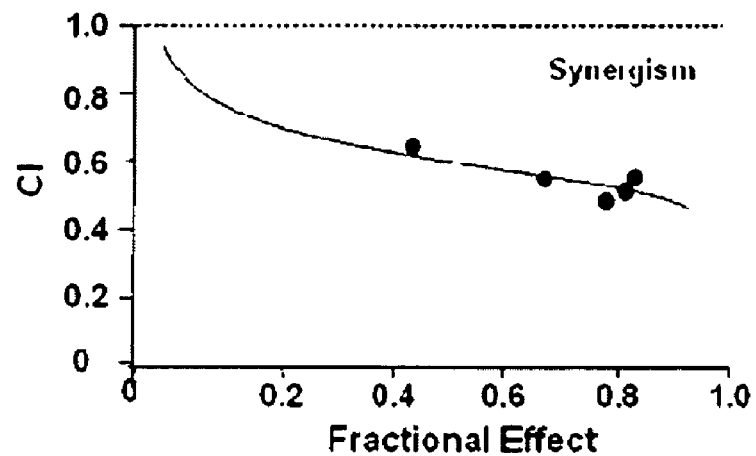
FIG. 2D. K562 cells were treated with the indicated concentrations of dasatinib and/or vorinostat for 48 hours. Following this, colony growth in semi-solid medium was assessed after 7 days. The values represent the mean % values of untreated control colony growth.

Combined treatment with vorinostat and dasatinib also induced synergistic apoptotic effects against K562 cells, as determined by the median dose effect isobologram analysis described by Chou and Talalay (FIG. 2C). For dasatinib and vorinostat, the combination index values were less than 1.0 in all cases. The CI values were 0.65, 0.55, 0.48, 0.51, and 0.56, respectively. Similar effect was noted against LAMA-84 cells (data not shown). The effects of dasatinib and vorinostat were also determined against normal bone marrow progenitor cells (NBMC's). While dasatinib (up to 20 nM) had no effect, exposure to 2.0 µM of vorinostat induced loss of survival of 15.9% of NBMC (mean of 2 samples with experiments performed in duplicate). This loss of survival was not augmented by co-treatment with 20 nM of dasatinib (data not shown). The inventors next determined the effects of dasatinib and/or vorinostat on the colony growth of K562 cells.

Figure 2D:
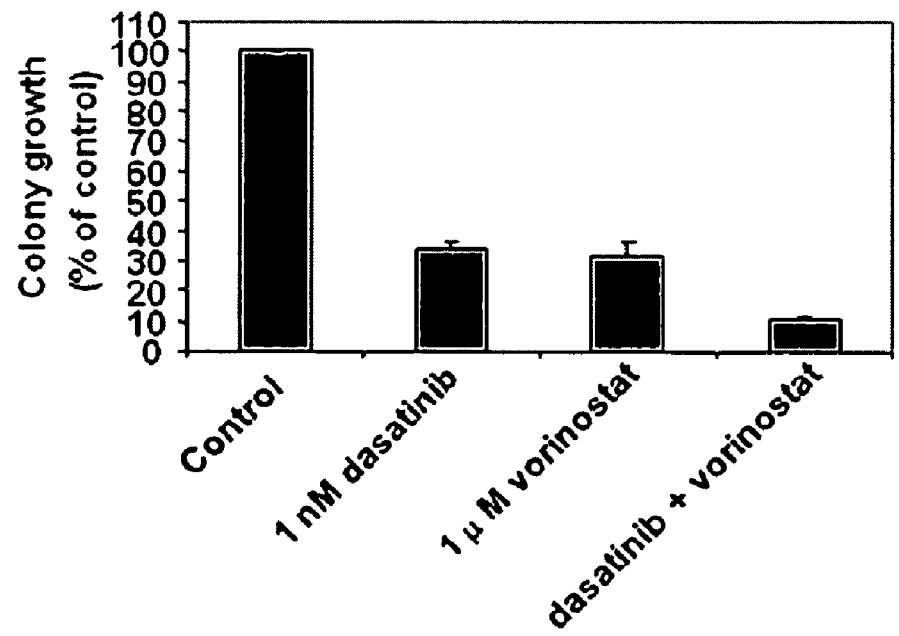
Figure 3:
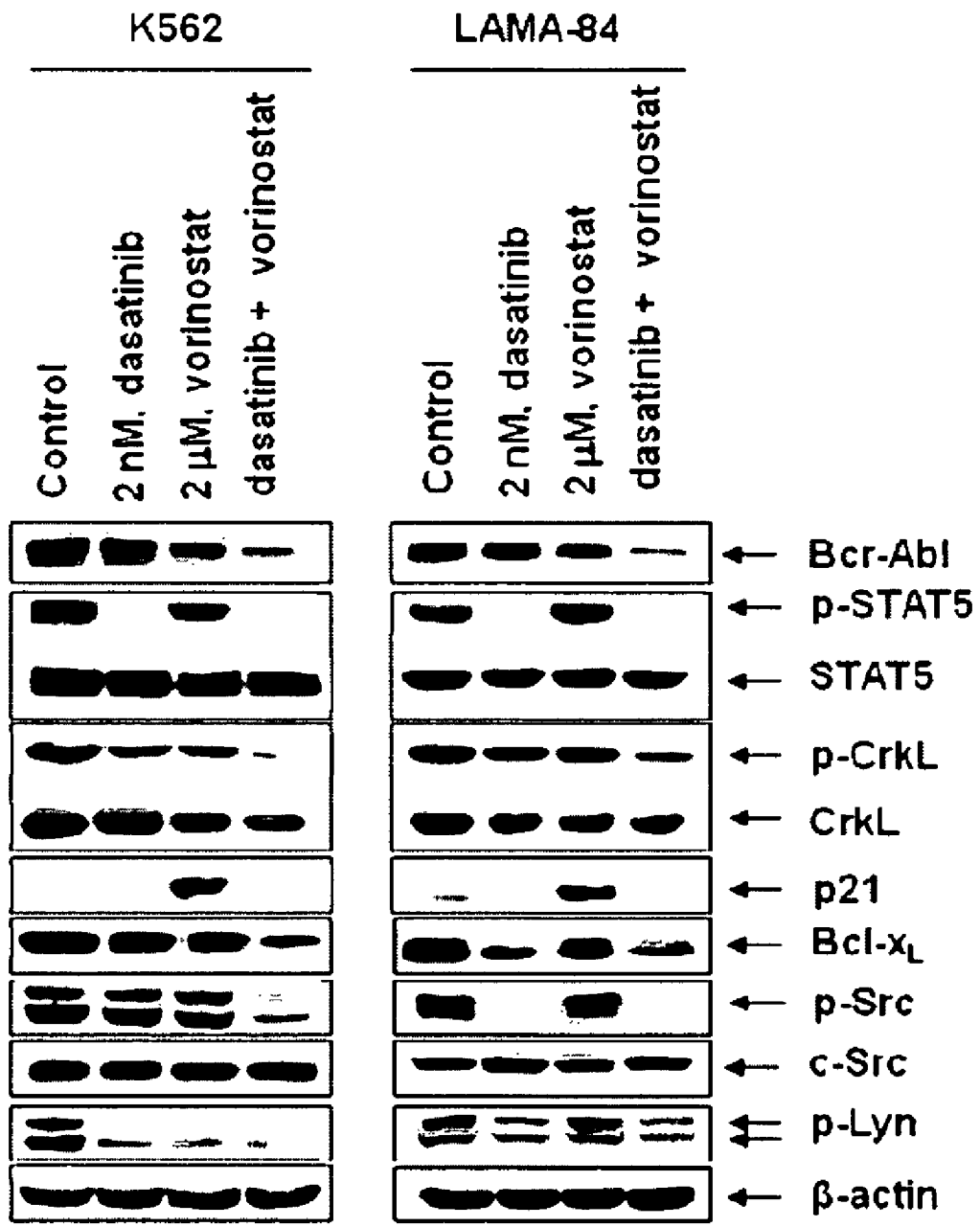
FIG. 3. Co-treatment with dasatinib and vorinostat enhances anti Bcr-Abl activity and attenuates levels of Bcr-Abl and p-CrkL greater than either agent alone in K562 than in LAMA-84 cells. Following treatment with 2 nM of dasatinib and/or 2 µM of vorinostat for 24 hours, Western blot analysis of Bcr-Abl, p-STAT5, STAT5, p-CrkL, CrkL, p21, Bcl-$x_L$, p-Src, p-Lyn, c-Src were performed on total cell lysates from K562 and LAMA-84. The levels of β-actin served as the loading control.

FIG. 2D demonstrates the surprising and unexpected results wherein co-treatment with dasatinib and vorinostat caused significantly more inhibition of colony growth than treatment with either drug alone (p<0.01). The inventors also determined that co-treatment with vorinostat enhances the effects of dasatinib on Bcr-Abl activity and on the downstream pro-growth and pro-survival signaling in K562 and LAMA-84 cells. As shown in FIG. 3, compared to treatment with either agent alone, co-treatment with vorinostat and dasatinib produced a greater decline in the levels of p-CrkL, in K562 and LAMA-84 cells. Combined treatment was also highly effective in lowering the levels of Bcl-xL, p-Src and p-Lyn. While vorinostat alone induced p21, co-treatment with dasatinib abrogated vorinostat-induced p21 levels.

Dasatinib and vorinostat induce apoptosis in BaF3 cells expressing unmutated or mutant Bcr-Abl.

Figure 4A:
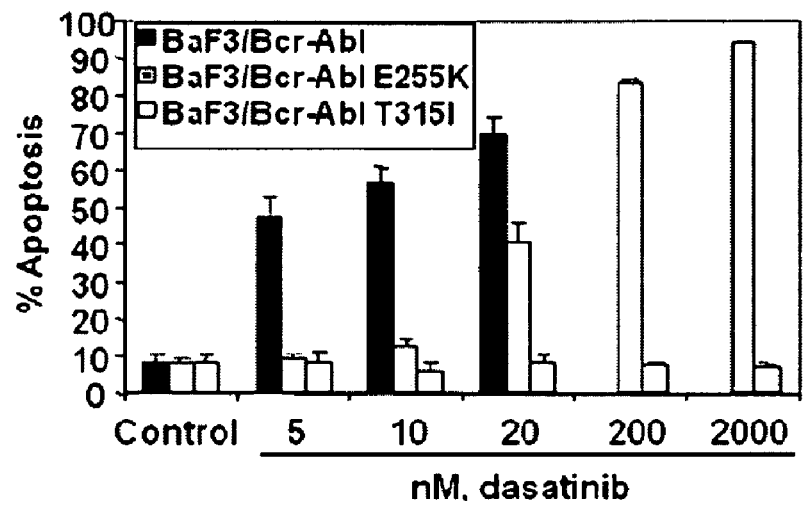
FIG. 4A. Treatment with dasatinib depletes Bcr-Abl activity and induces apoptosis of pro-B BaF3 cells with ectopic expression of unmutated or mutant Bcr-AblE255K but not of Bcr-AblT315I. BaF3 cells with ectopic expression of either unmutated or mutant Bcr-AblE255K or Bcr-AblT315I were treated with the indicated concentrations of dasatinib for 48 hours. After treatment, the percentage of Annexin-V-stained apoptotic cells was determined by flow cytometry. Values represented are the mean of three experiments±S.E.M. B. BaF3/Bcr-Abl and BaF3/Bcr-AblE255K cells were treated with the indicated concentrations of dasatinib for 24 hours.
Figure 4B:
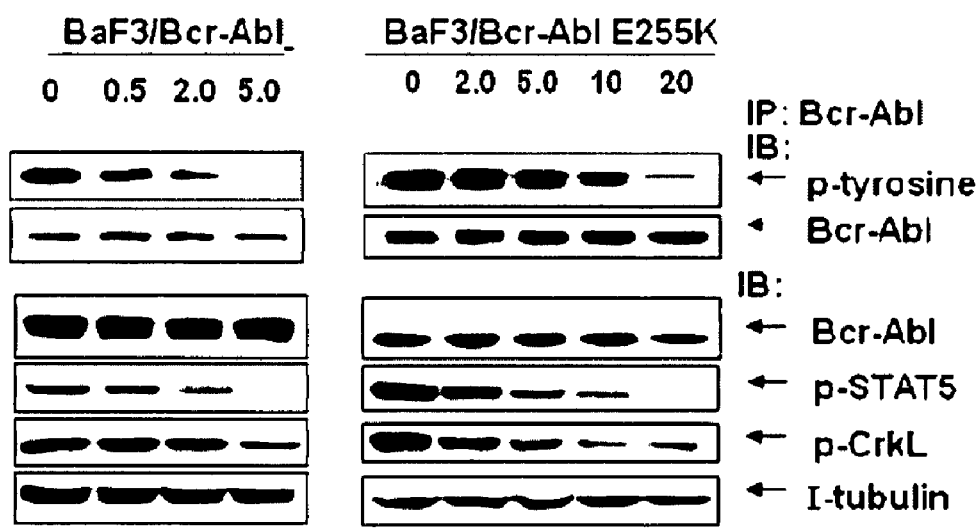
FIG. 4B. Following the procedure followed in FIG. 4A, Bcr-Abl was immunoprecipitated from total cell lysates and immunoblotted for tyrosine-phosphorylated Bcr-Abl. The blot was stripped and probed for total Bcr-Abl levels. Immunoblot analysis was performed for Bcr-Abl, p-STAT5, and p-CrkL in the total cell lysates from the same cells. The level of α-tubulin served as the loading control.
Figure 4C:
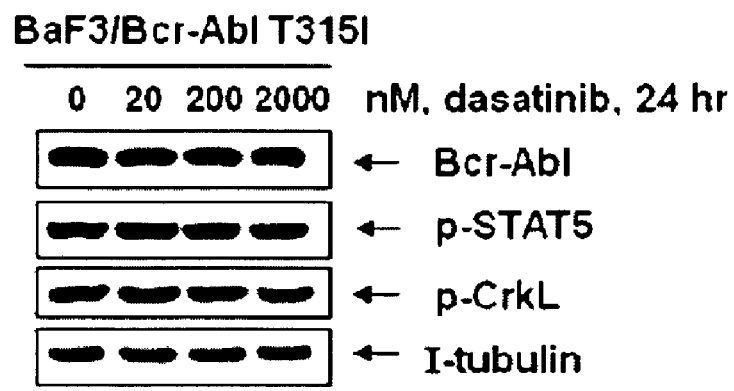
FIG. 4C. BaF3/Bcr-AblT315I cells were treated with the indicated concentrations of dasatinib for 24 hours. Following this, western blot analysis of Bcr-Abl, p-STAT5 and p-CrkL were performed on the total cell lysates. Levels of α-tubulin served as the loading control.
Figure 4D:
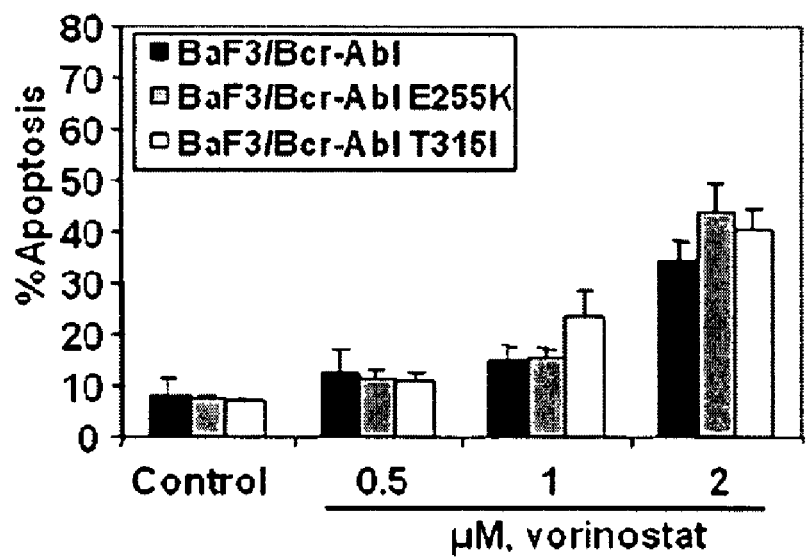
FIG. 4D. BaF3/Bcr-Abl, BaF3/Bcr-AblE255K, and BaF3/Bcr-AblT315I cells were treated with the indicated concentrations of vorinostat for 48 hours. After treatment, the percentage of Annexin-V-stained apoptotic cells was determined by flow cytometry. Values represented are the mean of three experiments±S.E.M.

Next, the inventors determined the effects of dasatinib and/or vorinostat in BaF3 cells with ectopic expression of either the unmutated Bcr-Abl or the point mutants Bcr-Abl E255K or Bcr-Abl T315I. Similar to the effects seen in K562 and LAMA-84 with endogenous expression of Bcr-Abl, treatment with 5.0 to 20 nM dasatinib induced apoptosis in BaF3/Bcr-Abl cells in a dose dependent manner (FIG. 4A). Following treatment with 20 nM of dasatinib, more than 70% of cells showed apoptosis. In contrast, BaF3/Bcr-AblE255K cells were relatively less sensitive to dasatinib-induced apoptosis, demonstrating a dose dependent increase in apoptosis at higher concentrations of dasatinib (20-2000 nM) (FIG. 4A). BaF3/Bcr-AblT315I cells were resistant to IM up to levels as high as 10 µM (data not shown). BaF3/Bcr-AblT315I-expressing cells were also resistant to apoptosis induced by high levels of dasatinib (2.0 µM). Treatment with dasatinib alone did not lower the levels of Bcr-Abl in BaF3 cells with ectopic expression of either the unmutated Bcr-Abl or the point mutants Bcr-Abl E255K or Bcr-Abl T315I. (FIGS. 4B and 4C). While exposure to 5.0 nM dasatinib markedly inhibited auto-phosphorylation of the unmutated Bcr-Abl, higher concentration of dasatinib (20 nM) achieved a similar effect against Bcr-AblE255K (FIG. 4B). Similarly, the higher dasatinib levels were required to attenuate p-STAT5 and p-CrkL levels in BaF3/Bcr-AblE255K versus BaF3/Bcr-Abl cells (FIG. 4B). Dasatinib did not appreciably inhibit autophosphorylation of Bcr-Abl (data not shown), or lower p-STAT5 and p-CrkL levels in BaF3/Bcr-AblT315I cells (FIG. 4C). On the other hand, in a dose dependent manner vorinostat induced apoptosis of not only BaF3/Bcr-Abl and BaF3/Bcr-AblE255K but also of BaF3/Bcr-AblT315I cells (FIG. 4D). Exposure to 2.0 µM of vorinostat resulted in apoptosis of approximately 40% of BaF3/Bcr-AblE255K cells (FIG. 4D). Notably, treatment with ≧1.0 µM vorinostat induced more apoptosis of BaF3/Bcr-AblT315I than of BaF3/Bcr-Abl cells. This is consistent with previous reports demonstrating that cells expressing the IM-resistant T315I point mutant are more sensitive to HA-HDIs than unmutated Bcr-Abl-expressing cells (36,37).

Co-treatment with vorinostat enhances dasatinib-induced apoptosis of IM-resistant BaF3 cells including those expressing Bcr-AblT315I.

Figure 5A:
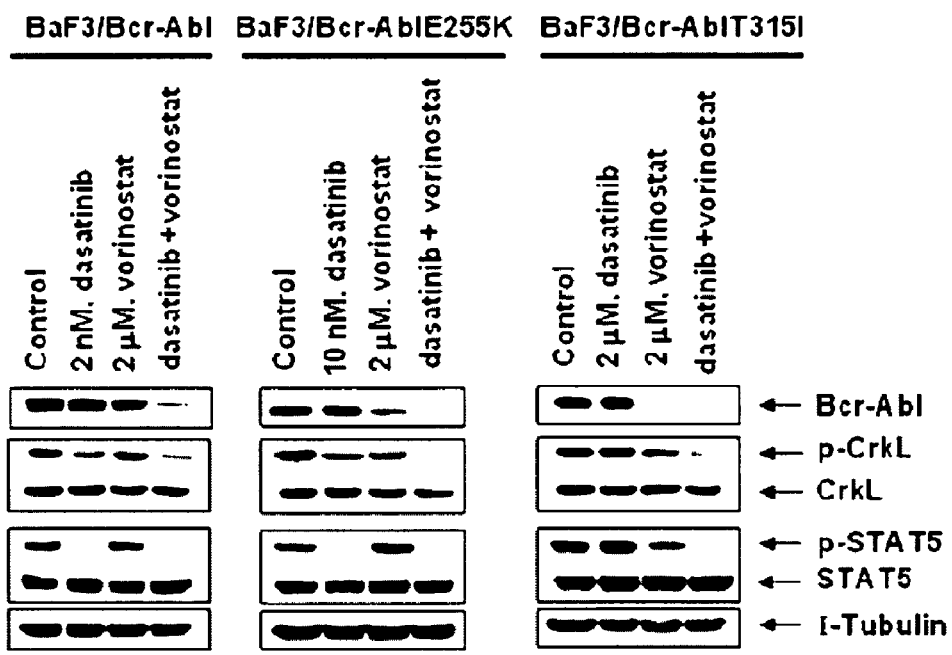
FIG. 5A. Co-treatment with dasatinib and vorinostat attenuates Bcr-Abl and p-CrkL levels greater than either agent alone and induces more apoptosis in BaF3/Bcr-Abl BaF3/Bcr-AblE255K and BaF3/Bcr-AblT315I cells. Cells were treated with the indicated concentrations of dasatinib and/or vorinostat for 24 hours. Western blot analysis was performed for Bcr-Abl, p-CrkL, CrkL, p-STAT5, and STAT5 on the total cell lysates from each cell line. The levels of α-tubulin served as the loading control.
Figure 5B:
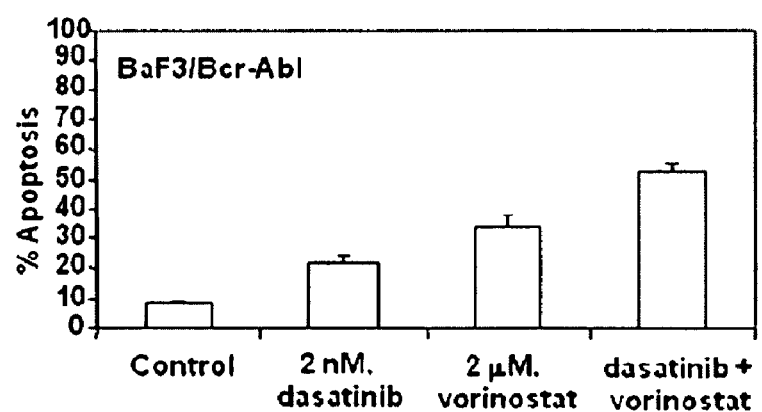
FIG. 5B-D. BaF3/Bcr-Abl, BaF3/Bcr-AblE255K, and BaF3/Bcr-AblT315I cells were treated with the indicated concentrations of dasatinib and/or vorinostat for 48 hours. Following treatment, the percentage of annexin-V-stained apoptotic cells was determined by flow cytometry. Values represented are the mean of three experiments performed in duplicate±S.E.M.
Figure 5C:
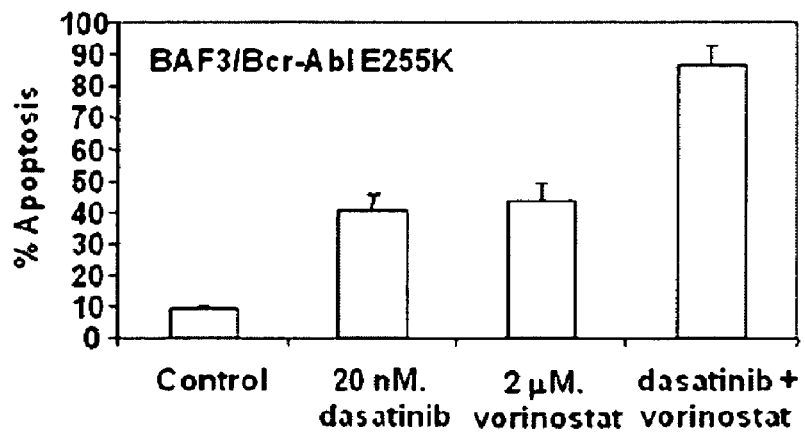
Figure 5D:
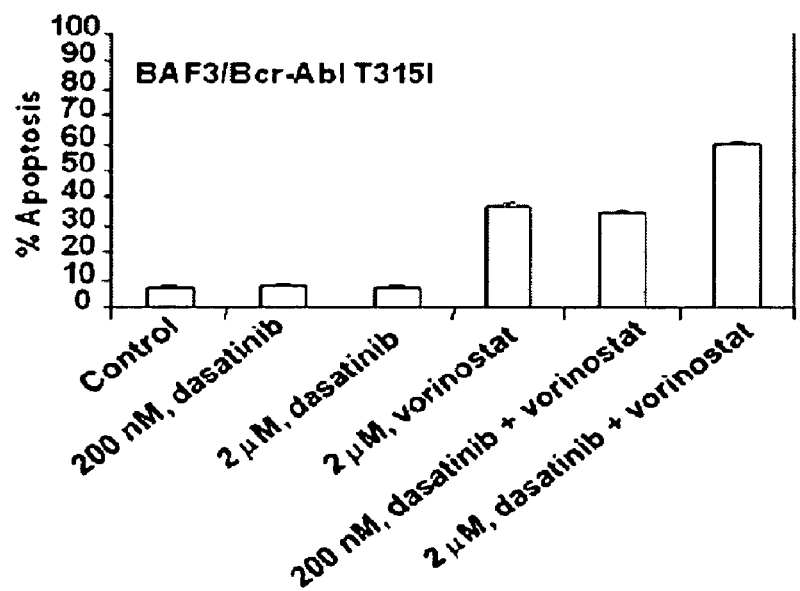

The inventors also determined the effects of treatment with vorinostat on the levels of Bcr-Abl and downstream signaling targets in BaF3/Bcr-Abl, BaF3/Bcr-AblE255K and BaF3/Bcr-AblT315I cells. Treatment of the BaF3 transfectants with vorinostat depleted Bcr-AblT315I>Bcr-AblE255K>unmutated Bcr-Abl levels (FIG. 5A). In contrast, exposure to up to 2.0 µM of dasatinib had no effect on the unmutated or mutant forms of Bcr-Abl (FIG. 5A and data not shown). Next, the inventors determined the effects of co-treatment with vorinostat and dasatinib on the levels of Bcr-Abl in BaF3/Bcr-Abl, BaF3/Bcr-AblE255K and BaF3/Bcr-AblT315I cells. As compared to treatment with either agent alone, combined treatment with vorinostat and dasatinib markedly depleted the levels of both of the mutant forms of Bcr-Abl in BaF3 cells. Based on the sensitivity to apoptosis to dasatinib noted in FIG. 4A, the inventors used higher concentrations of dasatinib in the combination against BaF3/Bcr-AblE255K and BaF3/Bcr-AblT315I cells (FIG. 5A). Co-treatment with vorinostat and dasatinib, more than either agent alone, also depleted the levels of p-STAT5 and p-CrkL in BaF3 cells with ectopic expression of unmutated Bcr-Abl, or of Bcr-AblE255K or Bcr-AblT315I (FIG. 5A). The mechanism underlying the striking decrease in p-STAT5 levels without any change in STAT5 levels is not obvious. However, it may be that co-treatment with the high levels of dasatinib employed in this experiment might render the upstream tyrosine kinase (responsible for phosphorylation of STAT5) more susceptible to depletion due to vorinostat mediated disruption of the chaperone function of hsp90 for the tyrosine kinase. Additionally, similar to the effects seen in K562 and LAMA-84 cells with endogenous expression of Bcr-Abl, co-treatment with vorinostat and dasatinib versus treatment with either agent alone induced significantly more apoptosis of BaF3/Bcr-Abl cells (FIG. 5B, p<0.05). Notably, combined treatment with vorinostat and dasatinib was also more effective than either agent alone in inducing apoptosis of BaF3/Bcr-AblT315I and BaF3/Bcr-AblE255K cells (FIGS. 5C and 5D). The combination induced apoptosis of approximately 90% of BaF3/Bcr-AblE255K and 60% of BaF3/Bcr-AblT315I cells (FIGS. 5C and 5D).

Co-treatment with dasatinib and vorinostat exerts unexpected and superior antileukemia activity against primary IM-resistant CML cells.

The inventors next determined the anti-leukemia effects of dasatinib and/or vorinostat against primary IM-resistant CML cells isolated from the peripheral blood and/or bone marrow from 11 patients who had relapsed with IM-resistant CML-BC (FIG. 6). Two of these samples were documented to express Bcr-Abl T315I (sample #10 and #11, FIG. 6). In the remaining samples of IM-resistant primary CML cells (samples #1 to #9, FIG. 6), due to inadequate sample size, the mutational status of Bcr-Abl could not be determined. FIG. 6 indicates that in the samples #1 to #9 dasatinib induced loss of cell viability in a dose dependent manner. Exposure to 2.0 µM vorinostat alone also induced loss of cell viability in all of the samples, including sample #10 and #11 (FIG. 6). Notably, while co-treatment with dasatinib and vorinostat induced more loss of cell viability in samples #1 to #9, in samples #10 and #11 addition of dasatinib did not augment the loss of cell viability due to treatment with vorinostat alone. One sample (CML#4) yielded sufficient cells for immunoprecipitation of Bcr-Abl to evaluate the effect of dasatinib and/or vorinostat on auto-phosphorylation and levels of Bcr-Abl, as well as on the levels of p-STAT5 and p-CrkL.

Figure 7A:
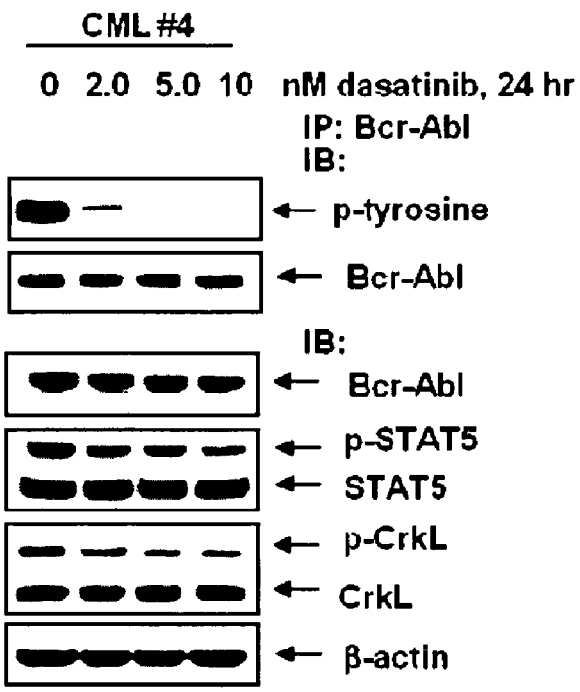
FIG. 7A. The effect of dasatinib and/or vorinostat on primary CML-BC cells. A. Primary CML cells were treated with the indicated concentrations of dasatinib for 24 hours. Bcr-Abl was immunoprecipitated from the total cell lysates and immunoblotted for tyrosine-phosphorylated Bcr-Abl. Blots were stripped and probed for total Bcr-Abl levels. Western blot analysis was performed for Bcr-Abl, p-STAT5, STAT5, p-CrkL, and CrkL on total cell lysates from the same cells. The levels of β-actin served as the loading control.
Figure 7B:
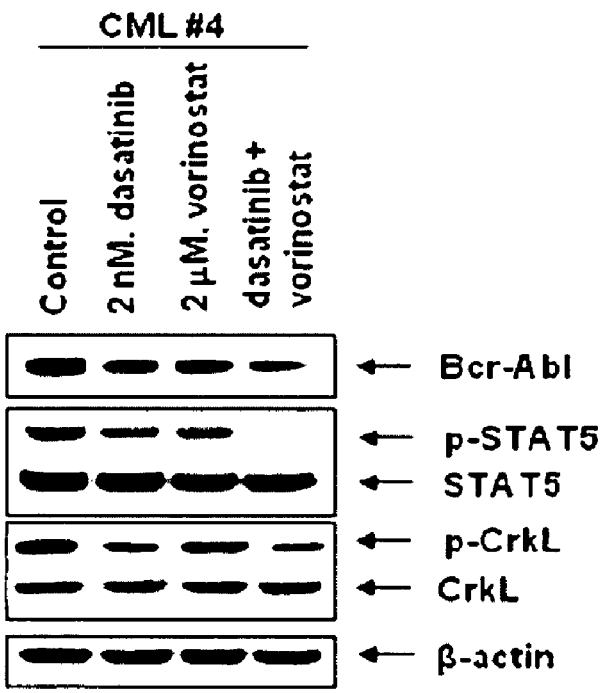
FIG. 7B. CML-BC cells were treated with dasatinib and/or vorinostat for 24 hours. After this, western blot analysis was performed for Bcr-Abl, p-STAT5, STAT5, p-CrkL and CrkL on the total cell lysates. The level of β-actin served as the loading control.

As was observed in K562 cells, dasatinib inhibited auto-phosphorylation of Bcr-Abl without affecting Bcr-Abl levels (FIG. 7A). Treatment with dasatinib also attenuated the levels of p-STAT5 and p-CrkL, with little effect on STAT5 and CrkL levels (FIG. 7A). While exposure of sample #4 cells to 2.0 µM vorinostat alone depleted the levels of Bcr-Abl, p-STAT5 and p-CrkL, co-treatment with dasatinib (2 nM) and vorinostat (2.0 µM) was even more effective than treatment with either agent alone in attenuating Bcr-Abl, p-STAT5 and p-CrkL (FIG. 7B). These findings are consistent with the increased lethality exerted against sample #4 cells by the combination of dasatinib (2 nM) and vorinostat (2.0 µM) (FIG. 7B). Treatment with dasatinib was clearly less effective in depleting the levels of p-STAT5 in the primary versus cultured CML cells.

Although the mechanisms underlying this disparity has not been elucidated, it is possible that in primary cells STAT5 phosphorylation may be mediated by the activity of Src as well as another tyrosine kinase(s), which is not inhibited by dasatinib.

Previous reports have separately described the activity of the pan-HDAC inhibitor vorinostat and the dual Abl/Src TK inhibitor dasatinib against Bcr-Abl expressing human CML cells. Here the inventors demonstrate for the first time that combined treatment with vorinostat and dasatinib is significantly more active than either agent alone against human CML cells with endogenous expression of the unmutated Bcr-Abl. Notably, the combination is also more active against BaF3 cells with ectopic expression of Bcr-Abl or its mutant isoforms Bcr-AblE255K or Bcr-AblT315I, as well as against IM-resistant human primary CML cells. Treatment with pan-HDAC inhibitors including vorinostat has been shown to inhibit the activity of HDAC6, which induces the acetylation of hsp90. This inhibits the ATP binding and chaperone function of hsp90, thereby disrupting the association of hsp90 with its client proteins, including Bcr-Abl, c-Raf and AKT. In turn, this promotes polyubiquitylation and proteasomal degradation of the client proteins. Vorinostat has also been shown to down modulate the levels of the Bcl-2 and the IAP family member proteins. Additionally, treatment with vorinostat upregulates the levels of Bim, a protein induced by the forkhead family of transcription factors that are repressed by phosphorylation by AKT. By attenuating c-Raf and in turn inhibiting the activity of the extracellular signal regulated kinase, which is known to phosphorylate Bim and diminish its association with Bcl-2 and Bcl-xL, vorinostat also promotes the pro-apoptotic effects of Bim. Collectively, these effects lower the threshold and promote vorinostat-induced apoptosis. The reported findings also explain why co-treatment with vorinostat sensitizes BaF3/Bcr-Abl and human CML cells to dasatinib-induced apoptosis.

That the combination of vorinostat and dasatinib induces more apoptosis of Bcr-Abl transformed cells is also consistent with several previous reports where co-treatment with a HA-HDI and a TK inhibitor, targeting a TK that is a bonafide hsp90 client protein (e.g. Bcr-Abl, Her-2 and FLT-3), was shown to induce more apoptosis than treatment with either agent alone. The inventor's findings demonstrate that, as compared to treatment with vorinostat alone, co-treatment with dasatinib mediates surprisingly more depletion of unmutated or mutant Bcr-Abl. Although the inventors do not have any experimental evidence to clarify the mechanism underlying this effect, it is possible that inhibition of Bcr-Abl activity and autophosphorylation may make it more susceptible to polyubiquitylation and proteasomal degradation due to vorinostat mediated disruption of the chaperone function of hsp90.

Recent studies have suggested that treatment with IM may be ineffective against CML stem cells, and acquired resistance to IM due to mutations in the Bcr-Abl kinase domain is a common occurrence. Amplification and increased expression of Bcr-Abl in CML progenitors may also confer IM resistance. Dasatinib is clearly a more potent inhibitor than IM of the unmutated Bcr-Abl TK activity, and dasatinib is also able to inhibit most of the mutant forms of Bcr-Abl. Vorinostat is shown here to not only deplete the levels of the un-mutated and mutant forms of Bcr-Abl, but also induces apoptosis of CML cells through Bcr-Abl independent mechanisms. This is important because IM-resistance may also be due to the dependence of CML cells for their growth and survival on signaling kinases other than Bcr-Abl, e.g., Lyn or MAPK. Therefore, the combination of vorinostat with dasatinib has the potential of overriding many if not all of the IM-resistance mechanisms in CML progenitor cells. Additionally, based on the multiple mechanism of activity noted above, the combination may also be able to override Bcr-Abl independent and Bcr-Abl-dependent resistance mechanisms prevalent in the CML stem cells. Mutations in the kinase domain of Bcr-Abl conferring IM resistance fall into two main groups, i.e., those inhibiting contact with IM and those that prevent Bcr-Abl from achieving the inactive conformation required for the binding of IM to Bcr-Abl. The point mutants Bcr-Abl E255K and Bcr-AblT315I have been recognized as the important and common examples of two groups of mutations that confer clinical resistance to IM. In the E255K mutation, which is located within the ATP binding region (P-loop) of the kinase domain of Bcr-Abl, glycine is replaced by lysine. This results in significant decrease in the sensitivity of Bcr-AblE255K to IM in the kinase assay and in conferring IM resistance on BaF3/Bcr-AblE255K cells. In Bcr-Abl the threonine 315 makes a hydrogen bond contact with IM, and a single nucleotide C to T change that results in a threonine to isoleucine substitution at this residue has been shown to confer high level of resistance to not only IM but also to dasatinib.

Recent pre-clinical studies have demonstrated that dasatinib is not only more potent in inhibiting unmutated Bcr-Abl TK but also active against most of the mutant forms of Bcr-Abl, except Bcr-AblT315I. It is noteworthy that treatment with hsp90 inhibitors has been reported to induce depletion of the mutant forms of Bcr-Abl and induce growth arrest and apoptosis of IM resistant CML cells. Indeed, mutant forms of Bcr-Abl appear to be more susceptible than unmutated Bcr-Abl to depletion induced by the hsp90 inhibitors. A similar observation has also been reported with respect to the mutant versus unmutated forms of other hsp90 client proteins, e.g., FLT-3. Vorinostat mediated inhibition of the chaperone function of hsp90 may be responsible for the depletion of the Bcr-AblE255K and Bcr-AblT315I levels in dasatinib treated BaF3/Bcr-AblE255K and BaF3/Bcr-AblT315I cells, respectively.

In early clinical trials, dasatinib has exhibited promising level of clinical activity in IM resistant CML. However, a substantial proportion of patients fail to achieve cytogenetic complete remission, especially in patients with more advanced phases of CML. Cells from these patients may harbor additional chromosomal abnormalities and genetic perturbations that often involve the recruitment of co-repressors and HDAC activity. This can potentially repress genes involved in differentiation and apoptosis. Co-treatment with vorinostat may override these mechanisms and sensitize leukemia cells to dasatinib-induced growth arrest and apoptosis, as was reported in the primary CML blast crisis cells. Additionally, co-treatment with vorinostat and dasatinib not only attenuates Bcr-Abl but also depletes the downstream, pro-growth and pro-survival signaling molecules, including p-AKT, p-ERK1/2 and p-STAT5. Accordingly, vorinostat may be exerting a 'longitudinal' two-step inhibition of the signaling initiated by Bcr-Abl, thus augmenting the growth inhibitory and apoptotic activity of dasatinib against CML-BC cells. A similar effect may explain the superior activity of the combination of an mTOR inhibitor and IM against CML cells. Co-treatment with vorinostat and dasatinib also caused more inhibition of p-STAT5, which was associated with more attenuation of the STAT5 target gene products Bcl-$x_L$ and c-Myc. Bcl-2 family members have been shown to act in a complementary manner to promote Bcr-Abl mediated induction of leukemia. Additionally, the inventor's findings demonstrate that vorinostat-mediated induction of p21 was blocked by co-treatment with dasatinib. This is consistent with previous reports, which have indicated that p21 induction decreased apoptosis induced by HDI, and interruption of HDI-induced p21 potentiates apoptosis due to treatment with HDI. Collectively, more dramatic inhibitory effects on several pro-growth and pro-survival signaling molecules may also contribute to the synergistic apoptotic effects of the combination of vorinostat and dasatinib in the cultured and primary CML cells. Since these findings have not been verified in vivo, the clinical significance of theses observations remains uncertain.

In the present studies vorinostat is shown to sensitize BaF3/Bcr-AblE255K and BaF3/Bcr-AblT315I cells to clinically achievable levels of dasatinib. Since at these levels, dasatinib is able to inhibit the Bcr-Abl TK activity of the mutant Bcr-AblE255K, it is likely that co-treatment with vorinostat enhances this activity of dasatinib by not only depleting the levels of Bcr-AblE255K but also due to other downstream mechanisms described above. However, the structural basis for how co-treatment with vorinostat leads to increased activity of relatively high levels of dasatinib (2.0 µM) against the contact inhibitory mutant Bcr-AblT315I is not entirely clear. It is also possible that vorinostat augments Bcr-Abl-independent growth inhibitory and cytotoxic mechanisms of dasatinib against Bcr-AblT315I expressing cells. However, further studies are needed to characterize these mechanisms. Alternatively, it is conceivable that vorinostat-mediated acetylation and inhibition of hsp90 chaperone function for Bcr-Abl affects its conformation in a manner that allows higher concentrations of dasatinib to interact with and inhibit Bcr-AblT315I. In a recent report, the non-ATP competitive Bcr-Abl kinase inhibitor ON012380 was shown to inhibit the activity of Bcr-AblT315I (62). It would also be important to determine whether co-treatment with vorinostat would further augment the activity of ON012380 against CML cells expressing Bcr-AblT315I.

As is known in the art, N-(2-chloro-6-methylphenyl)-2-[[6-[4-(2-hydroxyethyl)-1-piperazinyl]-2-methyl-4-pyrimidinyl]amino]-5-thiazolecarboxamide refers to a compound having the following structure (I):

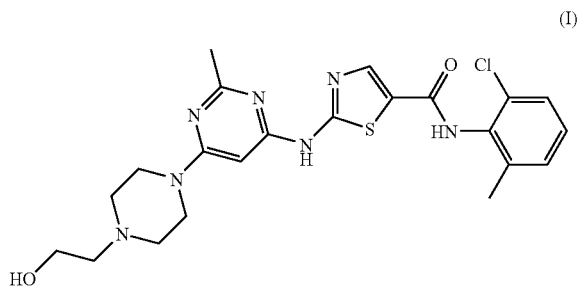

(I)

Compound (I) can also be referred to as N-(2-chloro-6-methylphenyl)-2-((6-(4-(2-hydroxyethyl)-1-piperazinyl)-2-methyl-4-pyrimidinyl)amino)-1,3-thiazole-5-carboxamide in accordance with IUPAC nomenclature. Compound (I) is also referred to herein as BMS-354825 and/or dasatinib. Use of the term "N-(2-chloro-6-methylphenyl)-2-[[6-[4-(2-hydroxyethyl)-1-piperazinyl]-2-methyl-4-pyrimidinyl]amino]-5-thiazolecarboxamide" encompasses (unless otherwise indicated) solvates (including hydrates) and polymorphic forms of the compound (I) or its salts (such as the monohydrate form of (I) described in U.S. Ser. No. 11/051,208, filed Feb. 4, 2005, incorporated herein by reference in its entirety and for all purposes). Pharmaceutical compositions of N-(2-chloro-6-methylphenyl)-2-[[6-[4-(2-hydroxyethyl)-1-piperazinyl]-2-methyl-4-pyrimidinyl]amino]-5-thiazolecarboxamide include all pharmaceutically acceptable compositions comprising N-(2-chloro-6-methylphenyl)-2-[[6-[4-(2-hydroxyethyl)-1-piperazinyl]-2-methyl-4-pyrimidinyl]amino]-5-thiazolecarboxamide and one or more diluents, vehicles and/or excipients, such as those compositions described in U.S. Ser. No. 11/402,502, filed Apr. 12, 2006, incorporated herein by reference in its entirety and for all purposes. One example of a pharmaceutical composition comprising N-(2-chloro-6-methylphenyl)-2-[[6-[4-(2-hydroxyethyl)-1-piperazinyl]-2-methyl-4-pyrimidinyl]amino]-5-thiazolecarboxamide is SPRYCEL™ (Bristol-Myers Squibb Company). SPRYCEL™ comprises N-(2-chloro-6-methylphenyl)-2-[[6-[4-(2-hydroxyethyl)-1-piperazinyl]-2-methyl-4-pyrimidinyl]amino]-5-thiazolecarboxamide as the active ingredient, also referred to as dasatinib, and as inactive ingredients or excipients, lactose monohydrate, microcrystalline cellulose, croscarmellose sodium, hydroxypropyl cellulose, and magnesium stearate in a tablet comprising hypromellose, titanium dioxide, and polyethylene glycol.

As is known in "BCR-ABL associated disorders" are those disorders which result from BCR-ABL activity, including mutant BCR-ABL activity, and/or which are alleviated by the inhibition of BCR-ABL, including mutant BCR-ABL, expression and/or activity. A reciprocal translocation between chromosomes 9 and 22 produces the oncogenic BCR-ABL fusion protein. The phrase "BCR-ABL associated disorders" is inclusive of "mutant BCR-ABL associated disorders".

Disorders included in the scope of the present invention include, for example, leukemias, including, for example, chronic myeloid leukemia, acute lymphoblastic leukemia, and Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia, chronic lymphocytic leukemia, mastocytosis and any symptom associated with mastocytosis. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia. Various additional cancers are also included within the scope of protein tyrosine kinase-associated disorders including, for example, the following: carcinoma, including that of the bladder, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma. In certain preferred embodiments, the disorder is leukemia, breast cancer, prostate cancer, lung cancer, colon cancer, melanoma, or solid tumors. In certain preferred embodiments, the leukemia is chronic myeloid leukemia (CML), Ph+ALL, AML, imatinib-resistant CML, imatinib-intolerant CML, accelerated CML, lymphoid blast phase CML.

A "solid tumor" includes, for example, sarcoma, melanoma, carcinoma, prostate carcinoma, lung carcinoma, colon carcinoma, or other solid tumor cancer.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ALL).

A "mutant BCR-ABL" encompasses a BCR-ABL tyrosine kinase with an amino acid sequence that differs from wild type BCR-ABL tyrosine kinase by one or more amino acid substitutions, additions or deletions. For example a substitution of the amino acid at position 255 or 315 of SEQ ID NO:2 with another amino acid would result in a mutant BCR-ABL tyrosine kinase.

"Mutant BCR-ABL associated disorder" is used to describe a BCR-ABL associated disorder in which the cells involved in said disorder are or become resistant to treatment with a kinase inhibitor used to treat said disorder as a result of a mutation in BCR-ABL. For example, a kinase inhibitor compound can be used to treat a cancerous condition, which compound inhibits the activity of wild type BCR-ABL which will inhibit proliferation and/or induce apoptosis of cancerous cells. Over time, a mutation can be introduced into the gene encoding BCR-ABL kinase, which can alter the amino acid sequence of the BCR-ABL kinase and cause the cancer cells to become resistant, or at least partially resistant, to treatment with the compound. Alternatively, a mutation can already be present within the gene encoding BCR-ABL kinase, either genetically or as a consequence of an oncogenic event, independent of treatment with a protein tyrosine kinase inhibitor, which can be one factor resulting in these cells propensity to differentiate into a cancerous or proliferative state, and also result in these cells being less sensitive to treatment with a protein tyrosine kinase inhibitor. Such situations are expected to result, either directly or indirectly, in a "mutant BCR-ABL kinase associated disorder" and treatment of such condition will require a compound that is at least partially effective against the mutant BCR-ABL, preferably against both wild type BCR-ABL and the mutant BCR-ABL. In the instance where an individual develops at least partial resistance to the kinase inhibitor imatinib, the mutant BCR-ABL associated disorder is one that results from an imatinib-resistant BCR-ABL mutation, or a protein tyrosine kinase inhibitor resistant BCR-ABL mutation. Similarly, in the instance where an individual develops at least partial resistance to the kinase inhibitor N-(2-chloro-6-methylphenyl)-2-[[6-[4-(2-hydroxyethyl)-1-piperazinyl]-2-methyl-4-pyrimidinyl]amino]-5-thiazolecarboxamide, the mutant BCR-ABL associated disorder is one that results from an N-(2-chloro-6-methylphenyl)-2-[[6-[4-(2-hydroxyethyl)-1-piperazinyl]-2-methyl-4-pyrimidinyl]amino]-5-thiazolecarboxamide resistant BCR-ABL mutation, or a protein tyrosine kinase inhibitor resistant BCR-ABL mutation. The present invention provides, among other things, methods of treating mutant BCR-ABL associated disorders and methods of identifying if an individual has a mutant BCR-ABL associated disorder.

If a BCR-ABL kinase mutation is found in the cells from said individual, treatment regimens can be developed appropriately. For example, an identified mutation can indicate that said cells are or will become at least partially resistant to commonly used kinase inhibitors. For example, a E255K or T315I mutation can indicate that the cells in an individual either are or are expected to become at least partially resistant to treatment with a kinase inhibitor such as N-(2-chloro-6-methylphenyl)-2-[[6-[4-(2-hydroxyethyl)-1-piperazinyl]-2-methyl-4-pyrimidinyl]amino]-5-thiazolecarboxamide. As disclosed herein, in such cases, treatment can include the use of an increased dosing frequency or increased dosage of N-(2-chloro-6-methylphenyl)-2-[[6-[4-(2-hydroxyethyl)-1- piperazinyl]-2-methyl-4-pyrimidinyl]amino]-5-thiazolecarboxamide or a salt, hydrate, or solvate thereof, a combination of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof and another kinase inhibitor drug such as imatinib, AMN107, PD180970, GGP76030, AP23464, SKI 606, and/or AZD0530; a combination of N-(2-chloro-6-methylphenyl)-2-[[6-[4-(2-hydroxyethyl)-1-piperazinyl]-2-methyl-4-pyrimidinyl]amino]-5-thiazolecarboxamide and a tubulin stabilizing agent (e.g., pacitaxol, epothilone, taxane, etc.); a combination of N-(2-chloro-6-methylphenyl)-2-[[6-[4-(2-hydroxyethyl)-1-piperazinyl]-2-methyl-4-pyrimidinyl]amino]-5-thiazolecarboxamide and a farnysyl transferase inhibitor; a combination of N-(2-chloro-6-methylphenyl)-2-[[6-[4-(2-hydroxyethyl)-1-piperazinyl]-2-methyl-4-pyrimidinyl]amino]-5-thiazolecarboxamide and a histone deacetylase inhibitor (e.g., Suberoylanalide Hydroxamic Acid); any other combination disclosed herein; and any other combination or dosing regimen comprising N-(2-chloro-6-methylphenyl)-2-[[6-[4-(2-hydroxyethyl)-1-piperazinyl]-2-methyl-4-pyrimidinyl]amino]-5-thiazolecarboxamide disclosed herein. In one aspect, an increased level of N-(2-chloro-6-methylphenyl)-2-[[6-[4-(2-hydroxyethyl)-1-piperazinyl]-2-methyl-4-pyrimidinyl]amino]-5-thiazolecarboxamide would be about 10, 20, 30, 40, 50, 60, 70, 80, 90, or 95% more than the typical N-(2-chloro-6-methylphenyl)-2-[[6-[4-(2-hydroxyethyl)-1-piperazinyl]-2-methyl-4-pyrimidinyl]amino]-5-thiazolecarboxamide dose for a particular indication or individual, or about 1.5×, 2×, 2.5×, 3×, 3.5×, 4×, 4.5×, 5×, 6×, 7×, 8×, 9×, or 10× more N-(2-chloro-6-methylphenyl)-2-[[6-[4-(2-hydroxyethyl)-1-piperazinyl]-2-methyl-4-pyrimidinyl]amino]-5-thiazolecarboxamide than the typical N-(2-chloro-6-methylphenyl)-2-[[6-[4-(2-hydroxyethyl)-1-piperazinyl]-2-methyl-4-pyrimidinyl]amino]-5-thiazolecarboxamide dose for a particular indication or for individual. Alternatively, an increased level of N-(2-chloro-6-methylphenyl)-2-[[6-[4-(2-hydroxyethyl)-1-piperazinyl]-2-methyl-4-pyrimidinyl]amino]-5-thiazolecarboxamide would be about 1.5×, 2×, 2.5×, 3×, 3.5×, 4×, 4.5×, 5×, 6×, 7×, 8×, 9×, or 10× more N-(2-chloro-6-methylphenyl)-2-[[6-[4-(2-hydroxyethyl)-1-piperazinyl]-2-methyl-4-pyrimidinyl]amino]-5-thiazolecarboxamide than the typical N-(2-chloro-6-methylphenyl)-2-[[6-[4-(2-hydroxyethyl)-1-piperazinyl]-2-methyl-4-pyrimidinyl]amino]-5-thiazolecarboxamide on a molar basis.

A therapeutically effective amount of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof can be orally administered as an acid salt of N-(2-chloro-6-methylphenyl)-2-[[6-[4-(2-hydroxyethyl)-1-piperazinyl]-2-methyl-4-pyrimidinyl]amino]-5-thiazolecarboxamide. The actual dosage employed can be varied depending upon the requirements of the patient and the severity of the condition being treated. Determination of the proper dosage for a particular situation is within the skill of the art. The effective amount of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof (and Compound I salt) can be determined by one of ordinary skill in the art, and includes exemplary dosage amounts for an adult human of from about 0.05 to about 100 mg/kg of body weight of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof, per day, which can be administered in a single dose or in the form of individual divided doses, such as from 1, 2, 3, or 4 times per day. In certain embodiments, N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof is administered 2 times per day at 70 mg. Alternatively, it can be dosed at, for example, 50, 70, 90, 100, 110, or 120 BID, or 100, 140, or 180 once daily. It will be understood that the specific dose level and frequency of dosing for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, and the like, subject to protein tyrosine kinase-associated disorders.

EXAMPLE

Dasatinib (BMS-354825) was kindly provided by Bristol-Myers Squibb (Princeton, N.J.). Vorinostat (SAHA; suberoylanilide hydroxamic acid) was kindly provided by Merck (Boston, Mass.). Monoclonal c-Abl antibody, polyclonal anti-STAT5A/B, polyclonal anti-Lyn, polyclonal anti-c-Src, monoclonal c-Myc and goat polyclonal anti-Pim-2 were purchased from Santa Cruz Biotechnology (Santa Cruz, Calif.). Monoclonal anti-p-STAT5 monoclonal anti-p27, monoclonal anti-Bcl-$x_L$ and monoclonal anti-phosphotyrosine were purchased from BD Biosciences (San Diego, Calif.). Polyclonal p-AKT was purchased from Biosource Inc (Camarillo, Calif.). Anti-phospho-c-Src and anti-phospho Lyn were purchased from Cell Signaling Technology (Beverly, Mass.). Antibodies for the immunoblot analyses of p21, p-CrkL, CrkL, AKT, Bim, Bcl-$x_L$ and ERK1/2 were obtained, as previously described (35-40).

Creation of BaF3/Bcr-Abl, BaF3/Bcr-AblE255K and BaF3/Bcr-AblT315I cell lines.

Mutant Bcr-Abl containing plasmids were generated by site-directed mutagenesis of pSTARp210Bcr-Abl or pSV-NeoBcr-Abl, as previously described. Briefly, the p210Bcr-AblE255K and p210Bcr-AblT315I constructs were created by site-directed mutagenesis of a Bcr-Abl containing pSV-Neo construct using a QuikChange II XL kit (Stratagene, Cedar Creek, Tex.) according to the manufacturer's recommendations, and the resulting clones were sequenced to confirm the point mutation. For nucleofection of the p210 Bcr-Abl constructs into BaF3 cells, five million BaF3 cells in 100 μL of Nucleofector solution V (Amaxa, Gaithersburg, Md.) were mixed with 5 g of either p210 Bcr-Abl WT, p210 Bcr-Abl (T315I), or p210 Bcr-Abl (E255K) in a cuvette and nucleofected using program G-16. Following nucleofection, the cells were incubated at a concentration of $1 \times 10^6$ cells/mL in complete RPMI-1640 media supplemented with 10% WEHI medium as the source of IL-3, overnight, to recover. Stable transfectants of Ba/F3 cells expressing the WT or mutant form of Bcr-Abl, i.e., T315I or E255K, were maintained in RPMI 1640 supplemented with 10% serum, 1.0 unit/ml penicillin, 1 μg/ml streptomycin, and 0.75 mg/ml G418. Stably expressing cells were then further selected by removal of IL-3. After confirmation of Bcr-Abl expression by immunoblot analysis, cells were used for the studies described below.

Cell Lines and Cell Culture.

Bcr-Abl-expressing, CML LAMA-84 and K562 cells were obtained and maintained in culture, as previously described. Logarithmically growing cells were exposed to the designated concentrations of dasatinib and/or vorinostat. Following these treatments, cells or cell pellets were washed free of the drug(s) prior to the performance of the studies.

Primary CML cells. CML cells from the peripheral blood and/or bone marrow of eleven patients who had met the clinical criteria of IM-resistant advanced phase of CML were harvested and purified, as previously described. Informed consents were signed by all patients to allow use of their cells for these experiments, as part of a clinical protocol approved by the University of South Florida Institutional Review Board (IRB).

Colony Growth Inhibition

Following treatment with the designated concentrations of dasatinib and/or vorinostat for 48 hours, untreated and drug treated cells were washed in RPMI-1640 medium. Following this, 200 cells treated under each condition were plated in duplicated wells in a 12-well plate containing 1.0 mL of Methocult media (Stem Cell Technologies, Inc., Vancouver, Canada) per well, according to the manufacturer's protocol. The plates were placed in an incubator at 37° C. with 5% $CO_2$ for 7 days. Following this incubation, colonies consisting of 50 or more cells in each well were counted with an inverted microscope and the % colony growth inhibition compared to the untreated control cells was calculated.

Cell Lysis and Protein Quantitation

Untreated or drug-treated cells were centrifuged and the cell pellets were resuspended in 200 µL of lysis buffer (1% Triton X-100, 1 mM phenylmethylsulfonyl fluoride (PMSF), 10 µg/ml leupeptin, 1 µg/ml pepstatin-A, 2 µg/ml aprotinin, 20 mM p-nitrophenyl phosphate, 0.5 mM sodium orthovanadate and 1 mM 4-(2-aminoethyl)benzenesulfonylfluoride hydrochloride) and incubated on ice for 30 minutes. The cell lysates were centrifuged and an aliquot of each cell lysate was diluted 1:10 and protein quantitated using a BCA protein quantitation kit (Pierce, Rockford, Ill.), according to the manufacturer's protocol.

Western Blot Analysis.

Western blot analyses of Bcr-Abl, p-STAT5, p-CrkL, p-Lyn, p-Src, STAT5, CrkL, c-Src, Lyn, p21, p27, Bcl-$x_L$, α-tubulin and β-actin were performed on total cell lysates using specific antisera or monoclonal antibodies, as previously described (35-40). The expression level of either β-actin or α-tubulin was used as the loading control for the Western blots.

Immunoprecipitation of Src and Bcr-Abl and Immunoblot Analysis

Following designated treatments, cells were lysed with the lysis buffer as described above. Bcr-Abl was immunoprecipitated from total cell lysates of untreated and drug-treated cells using a monoclonal anti-c-Abl antibody from Santa Cruz Biotechnologies (Santa Cruz, Calif.) and incubating at 4° C. for 1-2 hours on a rotator. Pre-washed protein-G beads were added to the lysate mixture and incubated overnight at 4° C. on a rotator. The immunoprecipitates were washed 4 times with lysis buffer and eluted from the agarose beads by boiling with 6×SDS sample buffer before immunoblot analysis. Total c-Src was immunoprecipitated from treated or untreated total cell lysates with a rabbit polyclonal antibody from Santa Cruz Biotechnologies (Santa Cruz, Calif.) and incubating at 4° C. for 1-2 hours on a rotator. Pre-washed protein-A beads were added to the lysate mixture and incubated overnight at 4° C. on a rotator. The immunoprecipitates were washed and eluted for SDS-PAGE, as above.

Src Kinase Assay

Ten million K562 or LAMA-84 cells were treated with dasatinib for 24 hours. One milligram of total cell lysate was used for immunoprecipitation of either Src or Lyn. For immunoprecipitation, 3 µg of anti-v-Src monoclonal antibody (Calbiochem, San Diego, Calif.) or 5 µg of anti-Lyn (Santa Cruz, Santa Cruz, Calif.) were incubated for 3 hours with the total cell lysate on a rotator at 4° C. Protein G beads were added to the lysate-antibody mixture and incubated on a rotator overnight at 4° C. The following day the agarose beads were washed 6 times with 500 µL of lysis buffer and once with 500 µL of 1× Kinase Buffer (100 mM Tris-HCl pH 7.2, 125 mM $MgCl_2$, 5 mM $MnCl_2$, 2 mM EGTA, 2 mM DTT and 250 µM $Na_3VO_4$). For the kinase reaction the beads were resuspended in 30 µL of IX kinase buffer. Ten micrograms of GST-purified Gab1CT and 10 µCi [$\gamma$-$^{32}$P] ATP (Perkin Elmer, Boston, Mass.) were added and the reaction was incubated at 30° C. for 15 minutes. The kinase reactions were terminated by adding 5 µL of 6×SDS sample buffer and boiling the samples for 5 minutes. The boiled samples were centrifuged briefly to pellet the agarose beads. The proteins were separated by SDS-PAGE, transferred to nitrocellulose and visualized by autoradiography.

Analysis of Cell Cycle Status

K562 or LAMA-84 cells were treated with dasatinib and/or vorinostat for 24 hours. Cells were washed and fixed in 70% ethanol overnight. Fixed cells were stained with propidium iodide and subjected to flowcytometry and analyses with ModFit 3.0.

Assessment of Apoptosis by Annexin-V Staining

Untreated or drug-treated cells were stained with Annexin-V (Pharmingen, San Diego, Calif.) and propidium iodide (PI) and the percentage of apoptotic cells were determined by flow cytometry. To analyze synergism between dasatinib and vorinostat in inducing apoptosis, K562 cells were treated with dasatinib (1-5 nmol/L) and vorinostat (1-5 µmol/L) at a constant ratio of 1:1000, respectively, for 48 hours. The percentage of apoptotic cells was determined by flow cytometry. The combination index (CI) for each drug combination was obtained by median dose effect of Chou and Talalay utilizing the combination index equation within the commercially available software Calcusyn (Biosoft, Ferguson, Mo.). CI values of less than 1.0 represent synergism of the two drugs in the combination.

Assessment of Percentage Non-Viable Cells

Cells were stained with trypan blue (Sigma, St. Louis, Mo.). The numbers of non-viable cells were determined by counting the cells that showed trypan blue uptake in a hemocytometer, and reported as percentage of untreated control cells.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed:

1. A method of inducing apoptosis in a cell comprising;
   contacting the cell with a therapeutically effective amount of a dual Abl/Src kinase inhibitor; and contacting the cell with a therapeutically effective amount of a histone deacetylase inhibitor.

2. The method of claim 1 wherein the dual Abl/Src kinase inhibitor is BMS-354825.

3. The method of claim 1 wherein the histone deacetylase inhibitor is suberoylanalide hydroxamic acid.

4. The method of claim 1 wherein the cell is a chronic myelogenous leukemia cell.

5. The method of claim 4 wherein the chronic myelogenous leukemia cell is in a stage selected from the group consisting of accelerated phase and blast crisis phase.

6. The method of claim 1 wherein the cell is resistant to imatinib mesylate.

7. The method of claim 1 wherein the cell contains a point mutation in the kinase domain in the bcr-abl gene.

8. The method of claim 7 wherein the point mutation in the kinase domain of Bcr-Abl is selected from the group consisting of T315I and E255K.

9. A method of treating a BCR-ABL-associated disorder comprising:
    obtaining a biological sample from an individual afflicted with a BCR-ABL-associated disorder;
    determining whether the biological sample obtained from the individual comprises a BCR-ABL polypeptide having at least one mutation wherein the at least one mutation is selected from the group consisting of a E255K and T315I mutation, wherein the presence of the at least one mutation is indicative of the patient being at least partially resistant to N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt, solvate, or hydrate thereof; and
    administering a therapeutically effective amount of N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt, solvate, or hydrate thereof, to the individual.

10. The method of claim 9 wherein the thiazolecarboxamide, or a pharmaceutically acceptable salt, solvate, or hydrate thereof, is administered at a higher dosage or dosing frequency if it is determined that the biological sample comprises a BCR-ABL polypeptide having the at least one mutation.

11. The method of claim 10 wherein the biological sample comprises a BCR-ABL polypeptide having the at least one mutation and the thiazolecarboxamide or pharmaceutically acceptable salt, hydrate, or solvate thereof is administered at a dosage of greater than 70 mg twice daily.

12. The method of claim 9 wherein the thiazolecarboxamide, or a pharmaceutically acceptable salt, solvate, or hydrate thereof, is administered in combination with an agent selected from the group consisting of a histone deacetylase inhibitor, a second protein tyrosine kinase inhibitor, second therapy, or a combination thereof.

13. The method of claim 12 wherein the histone deacetylase inhibitor is suberoylanalide hydroxamic acid.

14. The method of claim 12 wherein the second therapy is a tubulin stabilizing agent, a farnysyl transferase inhibitor, a BCR-ABL T315I inhibitor, or a combination thereof.

15. A method of attenuating the levels of point mutations in the Bcr-Abl kinase domain in a cell, comprising:
    contacting the cell with a therapeutically effective amount of a dual Abl/Src inhibitor; and
    contacting the cell with a therapeutically effective amount of a histone deacetylase inhibitor.

16. The method of claim 15 wherein the point mutation in the kinase domain of Bcr-Abl is selected from the group consisting of Bcr-AblE255K and Bcr-AblT315I.

17. The method of claim 15 wherein the dual Abl/Src kinase inhibitor is BMS-354825.

18. The method of claim 15 wherein the histone deacetylase inhibitor is Suberoylanalide Hydroxamic Acid.

19. The method of claim 15 wherein the cell is a chronic myelogenous leukemia cell in a stage selected from the group consisting of accelerated phase and blast crisis phase.

20. The method of claim 15 wherein the cell is resistant to imatinib mesylate.

\* \* \* \* \*

UNITED STATES PATENT AND TRADEMARK OFFICE
CERTIFICATE OF CORRECTION

| | |
|---|---|
| PATENT NO. | : 7,799,788 B2 |
| APPLICATION NO. | : 12/364009 |
| DATED | : September 21, 2010 |
| INVENTOR(S) | : Bhalla et al. |

It is certified that error appears in the above-identified patent and that said Letters Patent is hereby corrected as shown below:

Col. 1, line 12, insert the following:

--This invention was made with Government support under Grant No. W81XWH-05-1-0211 awarded by the United States Army Medical Research and Materiel Command (ARMY/MRMC). The Government has certain rights in the invention.--

Signed and Sealed this
Fourteenth Day of August, 2012

David J. Kappos
*Director of the United States Patent and Trademark Office*